United States Patent [19]
Saito et al.

[11] Patent Number: 5,489,430
[45] Date of Patent: Feb. 6, 1996

[54] POULTRY MYCOPLASMA ANTIGEN, GENE THEREOF AND RECOMBINANT VECTORS CONTAINING THE GENE AS WELL AS VACCINES UTILIZING THE SAME

[75] Inventors: Shuji Saito; Setsuko Ohkawa; Ayumi Fujisawa, all of Kanagawa; Yoshikazu Iritani, Kyoto; Shigemi Aoyama, Shiga, all of Japan

[73] Assignees: Nippon Zeon Co., Ltd., Tokyo; Shionogi & Co., Ltd., Osaka, both of Japan

[21] Appl. No.: 185,851

[22] PCT Filed: May 28, 1993

[86] PCT No.: PCT/JP93/00715

§ 371 Date: Jan. 25, 1994

§ 102(e) Date: Jan. 25, 1994

[87] PCT Pub. No.: WO93/24646

PCT Pub. Date: Dec. 9, 1993

[30] Foreign Application Priority Data

May 29, 1992 [JP] Japan ..................... 4-138819

[51] Int. Cl.$^6$ .................... A61K 39/02; C07K 14/30; C12N 15/31; C12N 1/21
[52] U.S. Cl. .................... 424/190.1; 424/192.1; 424/264.1; 530/350; 930/200; 536/23.7; 435/320.1; 435/252.3; 435/240.2; 435/252.31; 435/252.33
[58] Field of Search ............ 530/350; 424/190.1, 424/192.1, 264.1; 536/23.7; 435/320.1, 252.3, 240.2, 256.11; 930/200

[56] References Cited

FOREIGN PATENT DOCUMENTS

| 0345021 | 12/1989 | European Pat. Off. ........ C07K 13/00 |
| 63-84484 | 4/1988 | Japan . |
| 2-111795 | 4/1990 | Japan . |
| 2-167079 | 6/1990 | Japan . |

OTHER PUBLICATIONS

Inamine, J. M. et al. 1990, J. Bacteriol. vol. 172 pp. 504–506, Colleux, L. et al. 1986—Cell vol. 44 pp. 521–533.
Saito, S. et al. 1993, Vaccine vol. 11 pp. 1061–1066.

*Primary Examiner*—Mary E. Mosher
*Attorney, Agent, or Firm*—Armstrong, Westerman Hattori, McLeland & Naughton

[57] ABSTRACT

A highly effective vaccine for *Mycoplasma gallisepticum* infection utilizing a substantially pure protein capable of reacting with *Mycoplasma gallisepticum* immunized serum or *Mycoplasma gallisepticum* infected serum, having a molecular weight of about 40 kilodaltons encoded by DNA sequence derived from *Mycoplasma gallisepticum* and having a specific restriction enzyme map, or a protein functionally equivalent thereto.

7 Claims, 4 Drawing Sheets

E : EcoRI
∇ : EcoRV
G : BglII
Sac : SacI
X : XbaI
Ss : SspI
Sp : SpeI

\* SITE OF NUCLEOTIDE TO BE MUTATED

E : EcoRI
V : EcoRV
G : BglII
Sac : SacI
X : XbaI
Ss : SspI
Sp : SpeI

* SITE OF NUCLEOTIDE TO BE MUTATED

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1305 base pairs
( B ) TYPE: nucleic acid
( C ) STRANDEDNESS: double
( D ) TOPOLOGY: circular ( i i i ) HYPOTHETICAL: NO ( i x ) FEATURE:
( A ) NAME/KEY: CDS
( B ) LOCATION: 202..1308

( x i ) SEQUENCE DESCRIPTION: SEQ ID NO:1:

```
AAAAACATCA GATTGTTAAT CTGATATCTT TGCTTAAAAA AACACAAAAT CTTCTAACAA        60

AATCCTAAAT AAATAAGCCG TTAAATTAAC TAAAAAATTA AAAAAATGGT TTTTCTTATC       120

AACCAAAATT CTCTAGTAAT AAACGCTTAT TTATTTTTAT TTTTAGTCAT CTTTTAAGAT       180

ATAAATATAT CTTAATATTC T ATG AAT AAG AAA AGA ATC ATC TTA AAG ACT         231
                        Met Asn Lys Lys Arg Ile Ile Leu Lys Thr
                          1               5                  10

ATT AGT TTG TTA GGT ACA ACA TCC TTT CTT AGC ATT GGG ATT TCT AGC         279
Ile Ser Leu Leu Gly Thr Thr Ser Phe Leu Ser Ile Gly Ile Ser Ser
                 15                  20                  25

TGT ATG TCT ATT ACT AAA AAA GAC GCA AAC CCA AAT AAT GGC CAA ACC         327
Cys Met Ser Ile Thr Lys Lys Asp Ala Asn Pro Asn Asn Gly Gln Thr
             30                  35                  40

CAA TTA CAA GCA GCG CGA ATG GAG TTA ACT GAT CTA ATC AAT GCT AAA         375
Gln Leu Gln Ala Ala Arg Met Glu Leu Thr Asp Leu Ile Asn Ala Lys
         45                  50                  55
```

| | | | | | | | | | | | | | | | | |
|---|---|---|---|---|---|---|---|---|---|---|---|---|---|---|---|---|
| GCA | AGG | ACA | TTA | GCT | TCA | CTA | CAA | GAC | TAT | GCT | AAG | ATT | GAA | GCT | AGT | 423 |
| Ala | Arg | Thr | Leu | Ala | Ser | Leu | Gln | Asp | Tyr | Ala | Lys | Ile | Glu | Ala | Ser | |
| | 60 | | | | 65 | | | | | 70 | | | | | | |
| TTA | TCA | TCT | GCT | TAT | AGT | GAA | GCT | GAA | ACA | GTT | AAC | AAT | AAC | CTT | AAT | 471 |
| Leu | Ser | Ser | Ala | Tyr | Ser | Glu | Ala | Glu | Thr | Val | Asn | Asn | Asn | Leu | Asn | |
| 75 | | | | | 80 | | | | | 85 | | | | | 90 | |
| GCA | ACA | CTA | GAA | CAA | CTA | AAA | ATG | GCT | AAA | ACT | AAT | TTA | GAA | TCA | GCC | 519 |
| Ala | Thr | Leu | Glu | Gln | Leu | Lys | Met | Ala | Lys | Thr | Asn | Leu | Glu | Ser | Ala | |
| | | | | 95 | | | | 100 | | | | | 105 | | | |
| ATC | AAC | CAA | GCT | AAT | ACG | GAT | AAA | ACG | ACT | TTT | GAT | AAT | GAA | CAT | CCA | 567 |
| Ile | Asn | Gln | Ala | Asn | Thr | Asp | Lys | Thr | Thr | Phe | Asp | Asn | Glu | His | Pro | |
| | | | | 110 | | | | 115 | | | | | 120 | | | |
| AAT | TTA | GTT | GAA | GCA | TAC | AAA | GCA | CTA | AAA | ACC | ACT | TTA | GAA | CAA | CGT | 615 |
| Asn | Leu | Val | Glu | Ala | Tyr | Lys | Ala | Leu | Lys | Thr | Thr | Leu | Glu | Gln | Arg | |
| | | 125 | | | | | 130 | | | | | 135 | | | | |
| GCT | ACT | AAC | CTT | GAA | GGT | TTA | GCT | TCA | ACT | GCT | TAT | AAT | CAG | ATT | CGT | 663 |
| Ala | Thr | Asn | Leu | Glu | Gly | Leu | Ala | Ser | Thr | Ala | Tyr | Asn | Gln | Ile | Arg | |
| | 140 | | | | | 145 | | | | | 150 | | | | | |
| AAT | AAT | TTA | GTG | GAT | CTA | TAC | AAT | AAT | GCT | AGT | AGT | TTA | ATA | ACT | AAA | 711 |
| Asn | Asn | Leu | Val | Asp | Leu | Tyr | Asn | Asn | Ala | Ser | Ser | Leu | Ile | Thr | Lys | |
| 155 | | | | | 160 | | | | | 165 | | | | | 170 | |
| ACA | CTA | GAT | CCA | CTA | AAT | GGG | GGA | ATG | CTT | TTA | GAT | TCT | AAT | GAG | ATT | 759 |
| Thr | Leu | Asp | Pro | Leu | Asn | Gly | Gly | Met | Leu | Leu | Asp | Ser | Asn | Glu | Ile | |
| | | | | 175 | | | | | 180 | | | | | 185 | | |
| ACT | ACA | GTT | AAT | CGG | AAT | ATT | AAT | AAT | ACG | TTA | TCA | ACT | ATT | AAT | GAA | 807 |
| Thr | Thr | Val | Asn | Arg | Asn | Ile | Asn | Asn | Thr | Leu | Ser | Thr | Ile | Asp | Glu | |
| | | | 190 | | | | | 195 | | | | | 200 | | | |
| CAA | AAG | ACT | AAT | GCT | GAT | GCA | TTA | TCT | AAT | AGT | TTT | ATT | AAA | AAA | GTG | 855 |
| Gln | Lys | Thr | Asn | Ala | Asp | Ala | Leu | Ser | Asn | Ser | Phe | Ile | Lys | Lys | Val | |
| | | 205 | | | | | 210 | | | | | 215 | | | | |
| ATT | CAA | AAT | AAT | GAA | CAA | AGT | TTT | GTA | GGG | ACT | TTT | ACA | AAC | GCT | AAT | 903 |
| Ile | Gln | Asn | Asn | Glu | Gln | Ser | Phe | Val | Gly | Thr | Phe | Thr | Asn | Ala | Asn | |
| 220 | | | | | 225 | | | | | 230 | | | | | | |
| GTT | CAA | CCT | TCA | AAC | TAC | AGT | TTT | GTT | GCT | TTT | AGT | GCT | GAT | GTA | ACA | 951 |
| Val | Gln | Pro | Ser | Asn | Tyr | Ser | Phe | Val | Ala | Phe | Ser | Ala | Asp | Val | Thr | |
| 235 | | | | | 240 | | | | | 245 | | | | | 250 | |
| CCC | GTC | AAT | TAT | AAA | TAT | GCA | AGA | AGG | ACC | GTT | NNN | AAT | GGT | GAT | GAA | 999 |
| Pro | Val | Asn | Tyr | Lys | Tyr | Ala | Arg | Arg | Thr | Val | Xaa | Asn | Gly | Asp | Glu | |
| | | | | 255 | | | | | 260 | | | | | 265 | | |
| CCT | TCA | AGT | AGA | ATT | CTT | GCA | AAC | ACG | AAT | AGT | ATC | ACA | GAT | GTT | TCT | 1047 |
| Pro | Ser | Ser | Arg | Ile | Leu | Ala | Asn | Thr | Asn | Ser | Ile | Thr | Asp | Val | Ser | |
| | | | 270 | | | | | 275 | | | | | 280 | | | |
| NNN | ATT | TAT | AGT | TTA | GCT | GGA | ACA | AAC | ACG | AAG | TAC | CAA | TTT | AGT | TTT | 1095 |
| Xaa | Ile | Tyr | Ser | Leu | Ala | Gly | Thr | Asn | Thr | Lys | Tyr | Gln | Phe | Ser | Phe | |
| | | 285 | | | | | 290 | | | | | 295 | | | | |
| AGC | AAC | TAT | GGT | CCA | TCA | ACT | GGT | TAT | TTA | TAT | TTC | CCT | TAT | AAG | TTG | 1143 |
| Ser | Asn | Tyr | Gly | Pro | Ser | Thr | Gly | Tyr | Leu | Tyr | Phe | Pro | Tyr | Lys | Leu | |
| | 300 | | | | | 305 | | | | | 310 | | | | | |
| GTT | AAA | GCA | GCT | GAT | GCT | AAT | AAC | GTT | GGA | TTA | CAA | TAC | AAA | TTA | AAT | 1191 |
| Val | Lys | Ala | Ala | Asp | Ala | Asn | Asn | Val | Gly | Leu | Gln | Tyr | Lys | Leu | Asn | |
| 315 | | | | | 320 | | | | | 325 | | | | | 330 | |
| AAT | GGA | AAT | GTT | CAA | CAA | GTT | GAG | TTT | GCC | ACT | TCA | ACT | AGT | GCA | AAT | 1239 |
| Asn | Gly | Asn | Val | Gln | Gln | Val | Glu | Phe | Ala | Thr | Ser | Thr | Ser | Ala | Asn | |
| | | | | 335 | | | | | 340 | | | | | 345 | | |
| AAT | ACT | ACA | GCT | AAT | CCA | ACT | CAG | CAG | TTG | ATG | AGA | TTA | AAG | TTG | CTA | 1287 |
| Asn | Thr | Thr | Ala | Asn | Pro | Thr | Gln | Gln | Leu | Met | Arg | Leu | Lys | Leu | Leu | |
| | | | 350 | | | | | 355 | | | | | 360 | | | |
| AAA | TCG | TTT | TAT | CAG | GTT | | | | | | | | | | | 1305 |
| Lys | Ser | Phe | Tyr | Gln | Val | | | | | | | | | | | |
| | | 365 | | | | | | | | | | | | | | |

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:2:

TACGTTCTTC CTGGCAAACC TTACCACTAC TT    32

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

CTACAAAGAA CCTAAATATC A    21

(2) INFORMATION FOR SEQ ID NO:4:

(i) SEQUENCE CHARACTERISTICS:
        (A) LENGTH: 368 amino acids
        (B) TYPE: amino acid
        (D) TOPOLOGY: linear (ii) MOLECULE TYPE: protein (xi) SEQUENCE DESCRIPTION: SEQ ID NO:4:

```
                              Met Asn Lys Lys Arg Ile Ile Leu Lys Thr
                               1               5                  10

Ile Ser Leu Leu Gly Thr Thr Ser Phe Leu Ser Ile Gly Ile Ser Ser
                15                  20                  25

Cys Met Ser Ile Thr Lys Lys Asp Ala Asn Pro Asn Asn Gly Gln Thr
                30                  35                  40

Gln Leu Gln Ala Ala Arg Met Glu Leu Thr Asp Leu Ile Asn Ala Lys
            45                  50                  55

Ala Arg Thr Leu Ala Ser Leu Gln Asp Tyr Ala Lys Ile Glu Ala Ser
        60                  65                  70

Leu Ser Ser Ala Tyr Ser Glu Ala Glu Thr Val Asn Asn Asn Leu Asn
 75                  80                  85                  90

Ala Thr Leu Glu Gln Leu Lys Met Ala Lys Thr Asn Leu Glu Ser Ala
                95                 100                 105

Ile Asn Gln Ala Asn Thr Asp Lys Thr Thr Phe Asp Asn Glu His Pro
            110                 115                 120

Asn Leu Val Glu Ala Tyr Lys Ala Leu Lys Thr Thr Leu Glu Gln Arg
        125                 130                 135

Ala Thr Asn Leu Glu Gly Leu Ala Ser Thr Ala Tyr Asn Gln Ile Arg
        140                 145                 150

Asn Asn Leu Val Asp Leu Tyr Asn Asn Ala Ser Ser Leu Ile Thr Lys
155                 160                 165                 170

Thr Leu Asp Pro Leu Asn Gly Gly Met Leu Leu Asp Ser Asn Glu Ile
                175                 180                 185

Thr Thr Val Asn Arg Asn Ile Asn Asn Thr Leu Ser Thr Ile Asn Glu
            190                 195                 200

Gln Lys Thr Asn Ala Asp Ala Leu Ser Asn Ser Phe Ile Lys Lys Val
        205                 210                 215
```

-continued

| | | | | | | | | | | | | | | |
|---|---|---|---|---|---|---|---|---|---|---|---|---|---|---|
| Ile | Gln 220 | Asn | Asn | Glu | Gln 225 | Ser | Phe | Val | Gly | Thr | Phe 230 | Thr | Asn | Ala | Asn |
| Val 235 | Gln | Pro | Ser | Asn | Tyr 240 | Ser | Phe | Val | Ala | Phe 245 | Ser | Ala | Asp | Val | Thr 250 |
| Pro | Val | Asn | Tyr | Lys 255 | Tyr | Ala | Arg | Arg | Thr 260 | Val | Xaa | Asn | Gly | Asp 265 | Glu |
| Pro | Ser | Ser | Arg 270 | Ile | Leu | Ala | Asn | Thr 275 | Asn | Ser | Ile | Thr | Asp 280 | Val | Ser |
| Xaa | Ile | Tyr 285 | Ser | Leu | Ala | Gly | Thr 290 | Asn | Thr | Lys | Tyr | Gln 295 | Phe | Ser | Phe |
| Ser | Asn 300 | Tyr | Gly | Pro | Ser | Thr 305 | Gly | Tyr | Leu | Tyr | Phe 310 | Pro | Tyr | Lys | Leu |
| Val 315 | Lys | Ala | Ala | Asp | Ala 320 | Asn | Asn | Val | Gly | Leu 325 | Gln | Tyr | Lys | Leu | Asn 330 |
| Asn | Gly | Asn | Val | Gln 335 | Gln | Val | Glu | Phe | Ala 340 | Thr | Ser | Thr | Ser | Ala 345 | Asn |
| Asn | Thr | Thr | Ala 350 | Asn | Pro | Thr | Gln | Gln 355 | Leu | Met | Arg | Leu | Lys 360 | Leu | Leu |
| Lys | Ser | Phe 365 | Tyr | Gln | Val | | | | | | | | | | |

POULTRY MYCOPLASMA ANTIGEN, GENE THEREOF AND RECOMBINANT VECTORS CONTAINING THE GENE AS WELL AS VACCINES UTILIZING THE SAME

TECHNICAL FIELD

The present invention relates to antigen proteins of *Mycoplasma gallisepticum* infected to poultry;, recombinant vectors integrated with genes encoding to antigen proteins, hosts transformed by the vectors, as well as poultry vaccines for *Mycoplasma gallisepticum* infections utilizing the antigen proteins.

BACKGROUND

*Mycoplasma gallisepticum* infectious disease, that is one of the most serious infections on poultry such as chickens, etc., is characterized by chronic respiratory impairment accompanied by inflammation of the air sac in chicken. When chickens were infected with *Mycoplasma gallisepticum*, an egg-laying rate and a hatching rate of eggs produced by infected chickens are markedly reduced. As the result, shipping of eggs and egg-laying chickens decrease so that a considerable economic loss is caused. In addition, *Mycoplasma gallisepticum* infection induces the reduction in immunity so that chickens are liable to suffer from other infectious diseases to cause complication of severe infectious diseases. Furthermore, *Mycoplasma gallisepticum* is known to be a pathogen of sinusitis in turkeys.

The present inventors already found proteins react with antisera against *Mycoplasma gallisepticum* (Japanese Patent Application Laid-Open No. 2-111795). It is expected that these proteins would be useful as vaccines for preventing *Mycoplasma gallisepticum* infections, but in order to prepare more potent vaccines, it is desired to provide proteins having a higher activity.

DISCLOSURE OF THE INVENTION

As a result of extensive investigations to obtain more effective vaccines for preventing *Mycoplasma gallisepticum* infections, the present inventors have selected TMG-1 from the proteins disclosed in Japanese Patent Application Laid-Open No. 2-111795 Supra. It has then be found that addition of protein of about 11 kilodaltons to TMG-1 markedly increased the antigenicity of *Mycoplasma gallisepticum*, antisera induced using the addition product as antigen prevent the growth of *Mycoplasma gallisepticum*, and the protein described above can be expected to be useful as poultry vaccine for preventing *Mycoplasma gallisepticum* infections and also useful as diagnosis of *Mycoplasma gallisepticum* infections for poultry use. The present invention has thus come to be accomplished.

BEST MODE FOR PRACTICING THE INVENTION

According to a first aspect of the present invention, there is provided a protein which causes an antigen-antibody reaction with *Mycoplasma gallisepticum* poultry antisera and has a molecular weight of about 40 kilodaltons (hereinafter abbreviated as kd) encoded by DNA sequence having a restriction enzyme cleavage map shown in FIG. 1. According to a second aspect of the present invention, there is provided a DNA sequence which encodes the amino acid sequence (see SEQ ID NO:1. According to a third aspect of the present invention, there is provided a recombinant vector containing the DNA and a host transformed or transfected by the recombinant vector. According to a fourth aspect of the present invention, there is provided a poultry vaccine for preventing *Mycoplasma gallisepticum* infections, comprising the said protein as an effective component.

Figure 1:
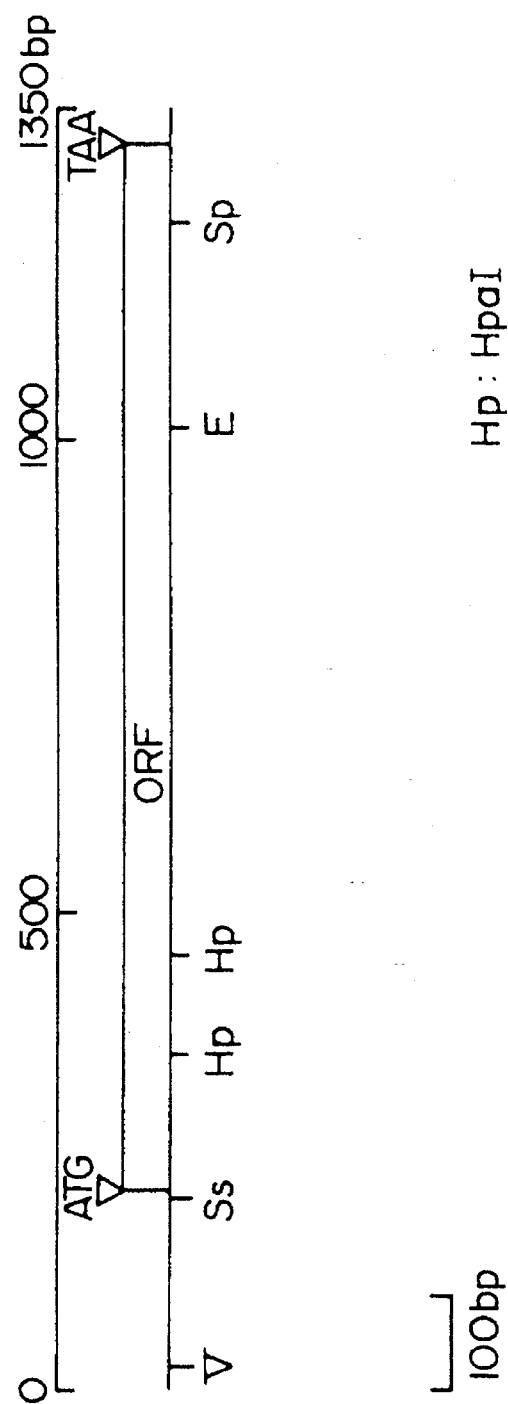
FIG. 1 shows a restriction enzyme cleavage map of DNA fragment which can be used for recombination in the present invention.

That is, in the first aspect of the present invention, the protein is the one that causes an antigen-antibody reaction with sera immunized or infected with *Mycoplasma gallisepticum* and has a molecular weight of about 40 Kd encoded by DNA sequence having a restriction enzyme cleavage map shown in FIG. 1. Specific examples include a protein having an amino acid sequence shown in Sequence No. 1, a fused protein having a C-terminus the amino acid sequence and containing bacteria-derived enzyme proteins such as β-galactosidase, β-lactamase, etc. at the N-terminus thereof.

The protein can be obtained by using the host transformed by or transfected by the recombinant vector that is concerned with the third aspect of the invention. The recombinant vector described above can be obtained by incorporating the DNA fragment as the third aspect of the invention into an expression vector in a conventional manner.

Figure 2:
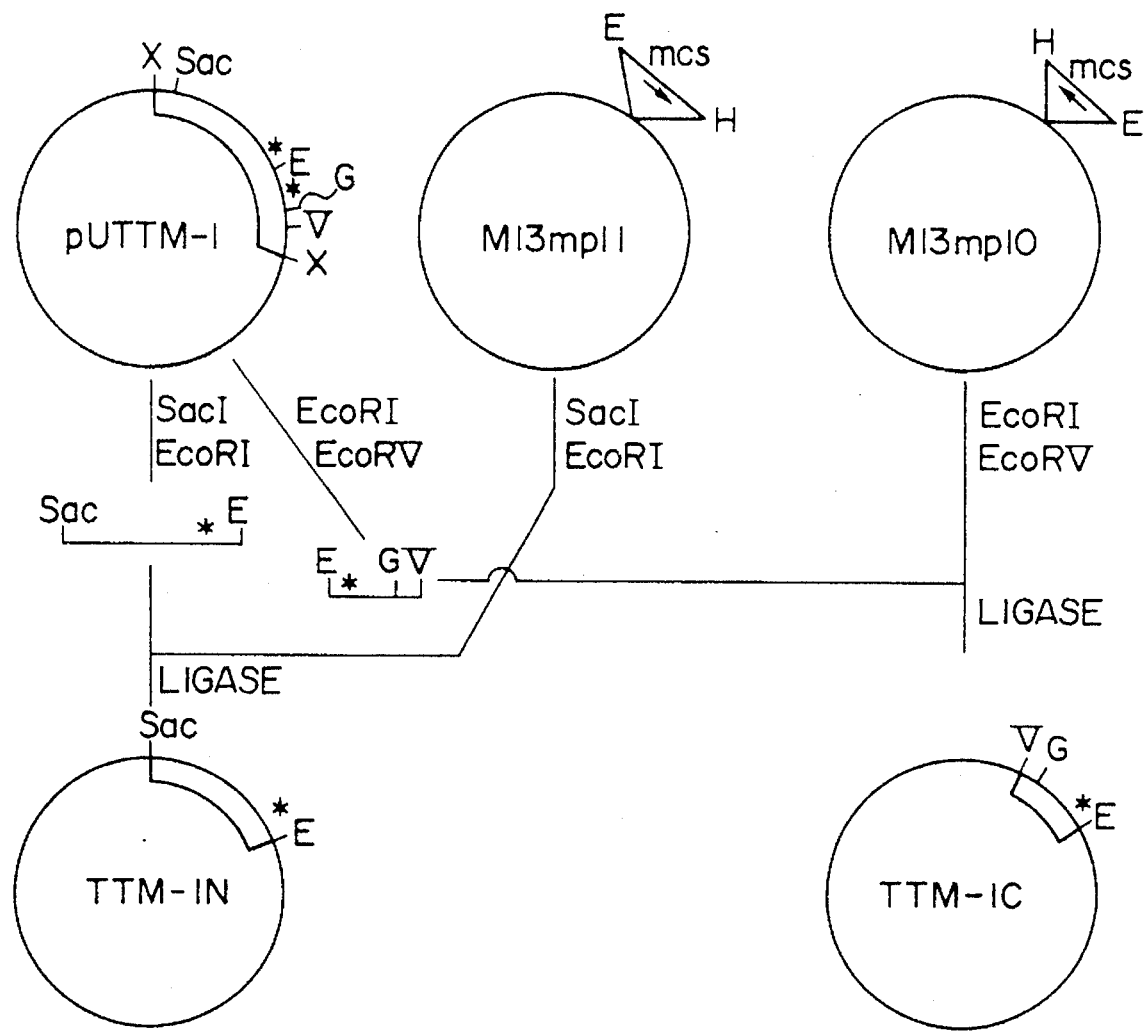
FIG. 2 illustratively shows the procedure for cloning TTM-1 DNA to M13 phage.
Figure 3:
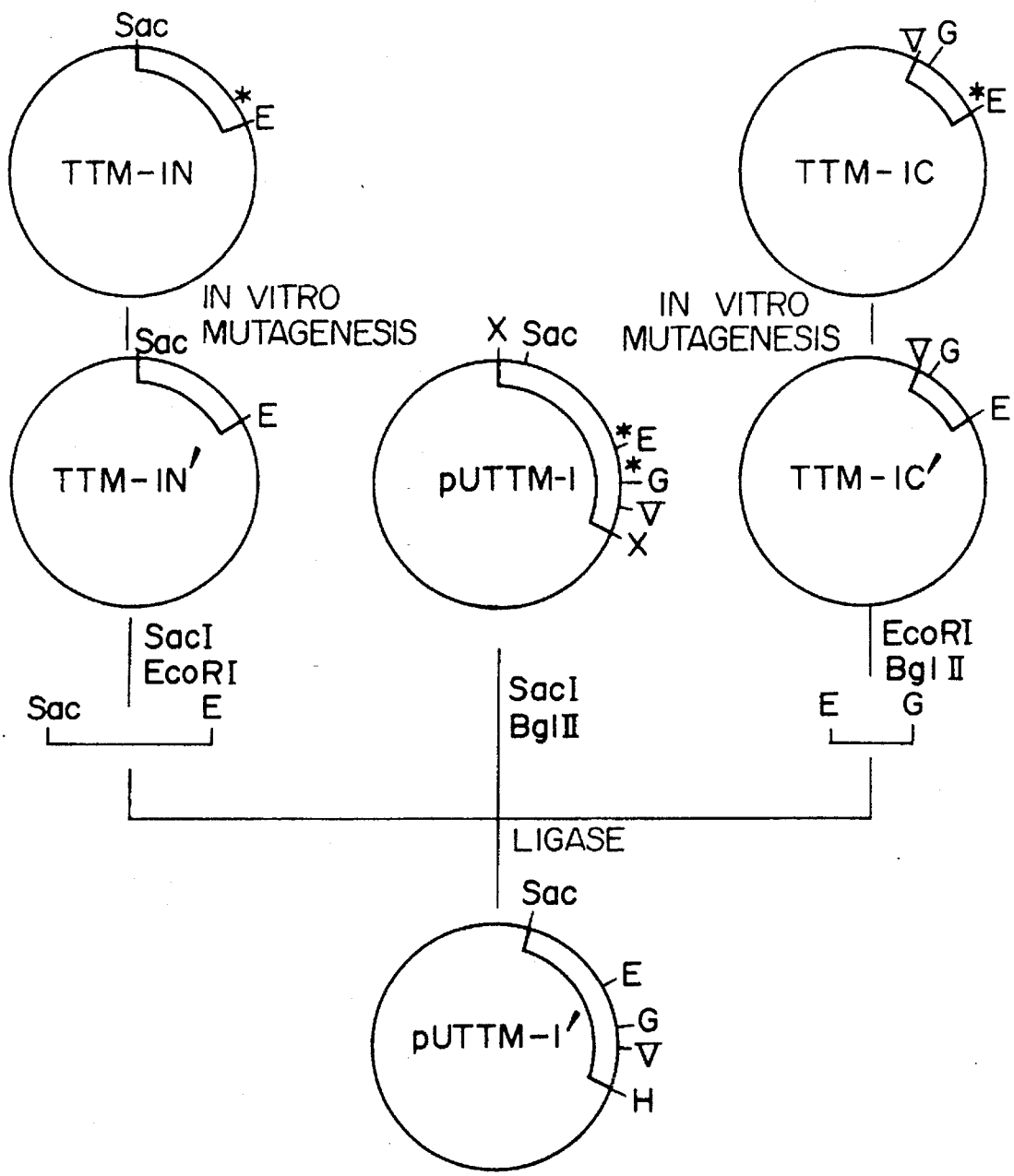
FIG. 3 illustratively shows the procedure for producing a site-specific mutant prepared using artificially synthesized oligonucleotide primer.
Figure 4:
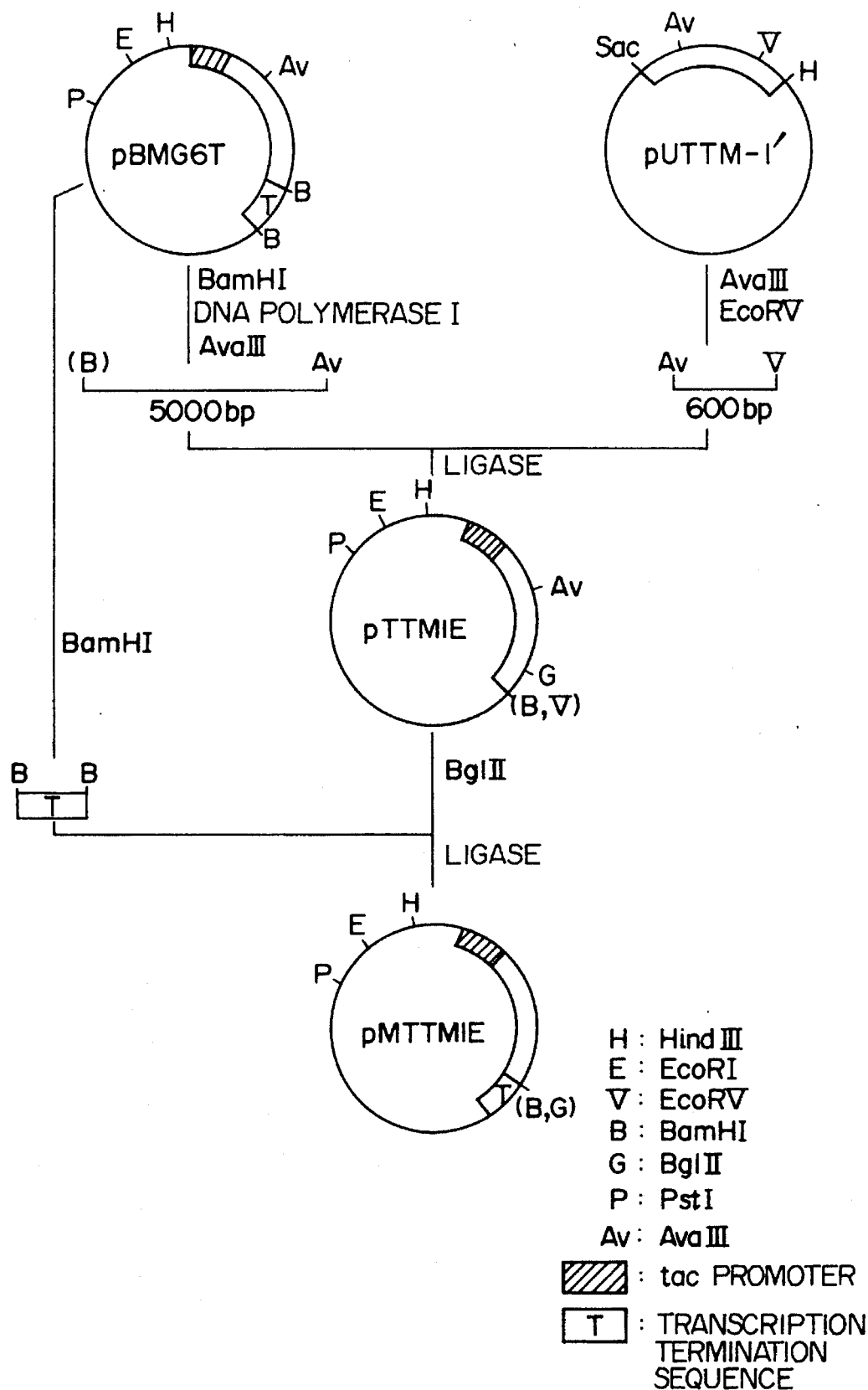
FIG. 4 illustratively shows the procedure for producing plasmid pMTTMIE which expresses protein TTMG-1 encoded by TTM-1'.

Sources for collecting the DNA fragment may be any of the sources so long as they belong to *Mycoplasma gallisepticum*. Specific examples include S6 strain (ATCC 15302), PG31 (ATCC 19610) and the like. Specific example of the DNA fragment used for recombination is a DNA fragment having a restriction enzyme cleavage map shown in FIG. 1 (for example, DNA fragment shown in FIG. 2.

The nucleotide sequence of 202 to 988 in the fragment having DNA sequence shown by Sequence No. 1 is the same as that of protein TMG-1 described in Japanese Patent Application Laid-Open No. 2-111795. The nucleotides of 986 to 988 which correspond to a termination codon of the gene encoding this TMG-1 are modified so as not to be translated as termination codon in the host, and DNA sequence of 999 to 1387 is further added thereto. TGA of 1048 to 1050 is also modified so as not to be translated as termination codon.

NNN in DNA sequence is not particularly restricted unless it is not a termination codon upon expression. However, it is expected in natural *Mycoplasma gallisepticum* that TGA would be translated into tryptophan (J. Bacteriology, 172(1), 504–506 (1990)). It is thus preferred to modify NNN into a base translated as tryptophan also in host cells, for example, into TGG.

The vector which is used to construct the recombinant vector is not particularly limited but specific examples include plasmids such as pUC8, pUC9, pUC10, pUC11, pUC18, pUC19, pBR322, pBR325, pBR327, pDR540, pDR720, and the like; phages such as λgt11, λgt10, λEMBL3, λEMBL4, Charon 4A and the like.

The method for inserting the DNA fragment described above into these vectors to produce recombinant vectors may be performed in a manner well known to one skilled in the art. For example, the vector is cleaved with a restriction enzyme and ligated directly with the DNA fragments described above, under control of a suitable expression regulatory sequence. As the expression regulatory sequence used, those may be mentioned, for example lac promoter-operator, trp promoter, tac promoter, lpp promoter, PL promoter, amyE promoter, Ga17 promoter, PGK promoter, ADH promoter, etc.

In producing the recombinant vector for the purpose of expressing these proteins derived from Mycoplasma, techniques for producing a recombinant vector by once incorporating the aforesaid DNA fragment into a suitable vector followed by subcloning is well known to one skilled in the art. These subcloned DNA fragment are excised with an appropriate restriction enzyme and ligated with the expression regulatory sequence described above to produce, the recombinant vector capable of producing the protein.

The vector which is used for the subcloning is not critical but specific examples include plasmids such as pUC8, pUC9, pUC10, pUC11, pUC18, pUC19, pBR322, pBR325, pBR327, PDR540, pDR720, pUB110, pIJ702, YEp13, YEp24, YCp19, pac373, pAcYM1, and the like.

Then, a variety of appropriate hosts are transformed using the obtained recombinant vector to obtain microorganisms that can produce the protein having antigenicity derived from *Mycoplasma gallisepticum*, or a fused protein containing the same amino acid sequence.

The appropriate host used herein can be chosen taking into account adaptability to expression vector, stability of the products, etc. Specific examples are genus Escherichia (for example, *Escherichia coli*), genus Bacillus (for example *Bacillus subtilis, Bacillus sphaericus*, etc.), Actinomyces, Saccharomyces, insect cell, silkworms, etc. The host transformed by an appropriate expression vector can be cultured and proliferated under suitable conditions well known to one skilled in the art.

Upon production of the protein, conditions for inducing the action of expression regulatory sequence can be chosen. More specifically, in the case of lac promoter-operator, such conditions can be effected by adding a suitable quantity of isopropylthio-β-D-galactopyranoside to a culture broth.

The poultry vaccine for *Mycoplasma gallisepticum* infections from the thus obtained host which is concerned with the fourth aspect of the invention can be prepared by a modification of conventional technique. The host can be cultured under conditions generally used for culturing microorganisms of this type. In the case of *E. coli*, the bacteria can be cultured in LB medium at 37° C. under aerobic conditions.

After culturing, the protein of the present invention as its first aspect can be purified by means of chromatography, precipitation by salting out, density gradient centrifugation and the like that are well known to one skilled in the art and may optionally be chosen. The thus obtained protein can be used as a vaccine. Alternatively, the transformed host can be inactivated and the inactivated host can be used as vaccine. In this case, the inactivation is carried out in a conventional manner after culture of the host is completed. The inactivation may be attained by heating but it is simpler to add an inactivator to the culture broth. As the inactivator, there may be used Merzonin, β-propiolactone, tyrosine, salicylic acid, Crystal Violet, benzoic acid, benzetonium chloride, polymyxin, gramicidin, formalin, phenol, etc. The inactivated culture broth is added, if necessary and desired, with a suitable quantity of adjuvant. The inactivated product is then separated with a siphon or by means of centrifugation, etc. As the adjuvant, aluminum hydroxide gel, aluminum phosphate gel, calcium phosphate gel, alum, etc., are employed. The inactivated product thus separated is adjusted with phosphate buffered saline, etc. to a suitable concentration. If necessary and desire, an antiseptic is added to the product. Examples of the antiseptic which can be used include Merzonin, β-propiolactone, tyrosine, salicylic acid, Crystal Violet, benzoic acid, benzetonium chloride, polymyxin, gramicidin, formalin, phenol, etc.

In order to further enhance the immune activity, adjuvant may also be added to the vaccine obtained. The adjuvant is generally used in a volume of 1 to 99 based on 100 volume of the vaccine.

When the vaccine is used, it may be mixed with diluents, thickeners, etc. in a conventional manner. The vaccine exhibits the effect in a dose of at least 1 μg antigenic protein mass per kg wt. The upper limit is not critical unless the dose shows acute toxicity. The dose can be determined opportunely, for example, under such conditions that the neutralizing antibody titer ($\log_{10}$) is 1.0 to 2.0. No acute toxicity was appreciable in a dose of 5 mg antigenic protein mass per kg wt. to chicken.

The poultry vaccine for *Mycoplasma gallisepticum* infection obtained in the present invention is inoculated to poultry intramuscularly, subcutaneously or intracutaneously, etc. The vaccine may also be sprayed onto respiratory tract for immunization.

According to the present invention, the proteins having higher antigenicity than those obtained in the prior art can be provided efficiently. The excellent peptides are effective as vaccines and poultry diagnostics for *Mycoplasma gallisepticum* infection.

EXAMPLES

Example 1

Harvest of polypeptide gene TTM-1 in which *Mycoplasma gallisepticum* is expressed:

(1) Production of genomic DNA of *Mycoplasma gallisepticum*

*Mycoplasma gallisepticum* S6 strain was cultured at 37° C. for 3 to 5 days in liquid medium prepared by supplementing 20% horse serum, 5% yeast extract, 1% glucose and a trace amount of phenol red as a pH indicator in 100 ml of PPLO broth basal medium. As *Mycoplasma qallisepticum* proliferated, pH of the culture broth decreased. At the point of time when the color of the pH indicator contained in the culture broth changed from red to yellow, incubation was terminated. The culture medium was centrifuged at 8000G for 20 minutes to collect the cells. The cells were then suspended in ⅒ volume of PBS based on the volume of culture medium. The suspension was again centrifuged at 10,000 rpm for 20 minutes to collect the cells. The collected cells were resuspended in 2.7 ml of PBS and SDS was added thereto in a concentration of 1%. Furthermore 10 μg of RNase was added to the mixture. The mixture was incubated at 37° C. for 30 minutes to cause lysis.

The lysate was extracted 3 times with an equal volume of phenol and then 3 times with ethyl ether. The extract was precipitated with ethanol to give 200 μg of genomic DNA of *Mycoplasma gallisepticum*.

(2) Genomic Southern hybridization of *Mycoplasma gallisepticum* using TM-1 gene as a probe After 1 μg of *Mycoplasma gallisepticum* DNA obtained in (1) was digested with XbaI, the digestion product was subjected to 0.6% low melting point agarose gel electrophoresis. After the electrophoresis, the gel was immersed in an alkali denaturing solution (0.5 M NaOH, 1.5 M NaCl) for 10 minutes to denature DNA and further immersed in a neutralizing solution (3 M sodium acetate, pH 5.5) for 10 minutes to neutralize. Following the neutralization, the DNA was transferred onto a nylon membrane in 6-fold SSC solution (0.7 M NaCl, 0.07 M sodium citrate, pH 7.5). After air drying, the membrane was heated at 80° C. for 2 hours. 4-fold SET (0.6 M NaCl, 0.08 M Tris-HCl, 4 mM EDTA, pH 7.8), 10-fold Denhardt, 0.1% SDS, 0.1% $Na_4P_2O_7$, 50 µg/ml of denatured salmon sperm DNA and pUM-1 insert DNA (TM-1 gene: see Japanese Patent Application Laid-Open No. 2-111795) which had been labelled in a conventional manner were added to cause hybridization at 68° C. for 14 hours. The nylon membrane was overlaid on an X ray film. Autoradiography revealed that hybridization occurred on a fragment of about 3.4 kbp.

(3) Cloning of XbaI-digested fragment of about 3.4 kbp into pUC-19 and colony hybridization After 4 µg of *Mycoplasma gallisepticum* DNA obtained in Example 1 (1) was digested with restriction enzyme XbaI, the digestion product was subject to 0.6% low melting point agarose gel electrophoresis. After the electrophoresis, a fragment of about 3.4 kbp was recovered. The fragment was ligated by ligase with pUC-19 cleaved through digestion with XbaI and competent *E. coli* TGl strain was transformed. The transformants were cultured at 37° C. for 15 hours in LB agar medium containing 0.003% of 5-bromo-4-Chloro-3-indolyl-β-Dgalactopyranoside, 0.03 mM of isopropylthio-β-Dgalactopyranoside and 40 μg/ml of ampicillin. White colonies grown on the agar medium were transferred onto a nylon membrane followed by hybridization in a manner similar to (2) above. Autoradiography revealed that cloning was effected and, the plasmid was named pUTTM1.

(4) Determination of the entire nucleotide sequence of TTM-1

Sequence of insert DNA fragment was determined by the Dideoxy method of Sanger et at. {Proc. Natl. Acad. Sci., USA, 74, 5463 (1977)} using pUTTM-1 prepared in (3) above. The nucleotide sequence is shown by Sequence No. 1 (provided that NNN in the sequence is both TGA). It is reported that TGA codon is read as tryptophan in the genus Mycoplasma, not as translation termination codon. In view of the sequence, the molecular weight of the protein encoded by TTM-1 was assumed to be about 40 kilodaltons.

Example 2

(1) Production of TTM-1' modified (TGA→TGG) not to read TTM-1-encoding protein TTMG-1 by TGA as translation termination codon ◎ 2-1 Cloning of TTM-1 DNA to M13 phage (FIG. 2)

pUTTM-1 of 1-(3) was digested with restriction enzymes SacI and EcoRI and the digestion product was then subjected to 0.8% low melting point agarose gel electrophoresis. A 1.1 kbp fragment containing the 5'-end of TTM-1 was recovered by treating with phenol-chloroform and precipitating with ethanol, followed by ligation with the fragment obtained by digestion of M13mp11 phage with SacI and EcoRI. The reaction solution was mixed at m.o.i. of 0.1 with a solution obtained by culturing *E. coli* TG1 at 37° C. for 24 hours, adding IPTG thereto in a final concentration of 100 mM and further supplementing IPTG in X-gal concentration of 2%. The resulting mixture was inoculated on soft agar to solidify. Incubation was then performed at 37° C. for 24 hours. Among the phage plaques formed, recombinant phage TTM-1N containing 1.1 kbp DNA of TTM-1 was collected from the phage, which color did not change to blue.

Likewise, pUTTM-1 was digested with EcoRI and EcoRV. After 0.8% low melting point agarose gel electrophoresis, a 0.4 kbp fragment containing the 3'-end of TTM-1 was recovered from the gel. By treating with phenol-chloroform and precipitating with ethanol, the DNA fragment was recovered. M13mp10 phage was ligated with the fragment obtained by digestion with EcoRI and EcoRV using ligase. The reaction solution was treated as in the cloning of 1 kbp DNA. Recombinant phage TTM-1C containing 0.4 kbp DNA of TTM-1 was thus obtained.

(2) Preparation of single stranded DNA from each recombinant phage

The two recombinant phage obtained in (1) above were added at m.o.i. of 0.1, respectively, to *E. coli* TG1 proliferated at 37° C. in 100 ml of 2 x YT medium. After shake culture at 37° C. for 5 hours, centrifugation was performed at 5000G for 30 minutes to obtain the cell-free supernatant. 0.2-fold volume of polyethylene glycol/sodium chloride mixture (20% polyethylene glycol #6000, 2.5 M NaC1) was added to the supernatant. After settlement at 4° C. for an hour, the mixture was centrifuged at 5000G for 20 minutes to recover the precipitates. The precipitates were dissolved in 500 −1 of TE buffer (10 mM Tris-HCl, 1 mM EDTA, pH 8.0). After extraction with phenol-chloroform, single stranded DNA of each recombinant phage was recovered by ethanol precipitation.

(3) Production of site-specific mutant using artificially synthesized oligonucleotide as a primer (FIG. 3)

When the thus obtained DNA is incorporated and expressed in *E. coli* as it is, the site corresponding to NNN of the nucleotides shown by Sequence No. 1 is recognized as termination codon since this portion is TGA. Thus, the sequences following the portion is not translated. Therefore, in order to modify nucleotide adenine corresponding to the third nucleotide of codon NNN to guanine, the following two oligonucleotides were synthesized to translate the TGA portion as methionine.

Sequence No. 2 (also referred to as SEQ ID NO:2):

3'-TACGTTCTTCCTGGCAAACCTTACCACTACTT-5' and,

Sequence No. 3 (also referred to as SEQ ID NO:3):

3'-CTACAAAGAACCTAAATATCA-5'

The oligonucleotide shown by Sequence No. 2 is annealed to single stranded DNA of TTM-1N and the oligonucleotide shown by Sequence No.3 to single stranded DNA of TTM-1C to cause the desired mutation by the method of Frits Eckstein et al. (Nucleic Acid Research, 8749–8764, 1985). The thus obtained recombinant phages were named TTM-1N' and TTM-1C', respectively. DNAs of TTM-1N' and TTM-1C' phages obtained were digested with restriction enzymes SacI-EcoRI and EcoRI-BglII, respectively. By 0.8% low melting point agarose gel electrophoresis, the fragments of 1.1 kbp and 0.4 kbp were extracted from the agarose gel and recovered by ethanol precipitation. On the other hand, plasmid pUTTM-1 was also digested with SacI-BglII. The 4.8 kbp fragment bearing vector was extracted by 0.8% low melting point agarose gel electrophoresis and recovered by ethanol precipitation. The thus obtained three fragments were ligated by ligase and competent *E. coli* TG1 strain was transformed to obtain plasmid pUTTM-1' bearing TTM-1' with mutation at the desired site thereof. Sequencing analysis was performed as in 1-(4). It was thus confirmed that the desired site underwent mutation.

The restriction enzyme map of the thus obtained gene derived from *Mycoplasma gallisepticum* is shown in FIG. 1.

Example 3

Production of expression plasmid pUTM1E of protein TTMG-1 encoded by TTM-1' (FIG. 4)

Digestion of plasmid pBMG6T (Japanese Patent Application Laid-Open No. 2-111795) with restriction enzyme BamHI was followed by a treatment with DNA polymerase I and then digestion with restriction enzyme AvaIII. After 0.8% low melting point agarose gel electrophoresis, DNA of about 5000 bp was recovered from the gel. By treating with phenol-chloroform and precipitation with ethanol, a fragment containing tac promoter was recovered. On the other hand, plasmid pUTTM1 obtained in (3) was digested with restriction enzymes AvaIII and EcoRV. The digestion product was subjected to 0.8% low melting point agarose gel electrophoresis. DNA of about 600 bp was recovered from the gel and treated with phenol-chloroform. By ethanol precipitation, a fragment containing a part of TTM-1 DNA was recovered.

The two fragments were ligated using ligase and competent *E. coli* TG1 strain was transformed. The transformants were cultured at 37° C. for 15 hours in LB agar medium containing ampicillin. The plasmid was extracted by the method of Birnboim & Doly [Nucleic Acid Research, 7, 1513 (1979)] to produce plasmid pTTM1E bearing tac promoter and TTM-1 DNA.

On the other hand, pBMG6T was digested with restriction enzyme BamHI. After 0.8% low melting point agarose gel electrophoresis, a fragment of about 700 bp containing transcription termination sequence was recovered by ethanol precipitation.

Lastly, pTTM1E was digested with restriction enzyme BglII followed by a treatment with phenol and chloroform. The fragment recovered by ethanol precipitation was ligated by ligase with the aforesaid fragment of about 700 bp containing the transcription termination sequence. The desired plasmid was selected in a manner similar to pTTM1E and named pMTTM1E.

Example 4

Expression of polypeptide encoded by TTM1E

After *E. coli* TG1 strain transformed by pMTTM1E was cultured at 37° C. for 12 hours in LB medium supplemented with 50 μl/ml of ampicillin, 1 ml of the culture broth was taken and added to 100 ml of LB medium containing 50 μg/ml of ampicillin followed by incubation at 37° C. Two hours later, 1 mM of isopropylthio-β-Dgalactopyranoside was added in a concentration of 1 mM and incubation was continued at 37° C. for further 12 hours. After the incubation, *E. coli* was centrifuged at 6000G for 10 minutes. After the cells were collected, the cells were subjected to 10% SDS-PAGE and electrophoresed at 50 mA for 2 hours. After the electrophoresis, the gel was stained with Coomassie Brilliant Blue R-250 thereby to detect a new band of about 40 kilodaltons, amounting to about 10% of the total cell protein. Since this molecular weight of the protein coincided with the estimated value, the protein having about 40 kilodaltons is identified to be the protein encoded by TTM-1 and named TTMG-1.

Furthermore, the gel thus applied on SDS-PAGE was transferred onto a nitrocellulose membrane for Western blotting [Towbin et al., Proc. Natl. Acad. Sci. USA, 76, 4350 (1979)] and as a primary antibody, chicken serum immunized with *Mycoplasma gallisepticum* was used, whereby a band of about 40 kd stained with Coomassie Brilliant Blue R-250 was reacted. It was thus confirmed that TTMG-1 was derived from *Mycoplasma gallisepticum*.

Example 5

Purification of TTMG-1

After *E. coli* collected in Example 4 were suspended in 10 ml of Dulbecco's PBS, the suspension was treated with French press (manufactured by Otake Seisakusho: 1500 kgf/cm2). Then, centrifugation was performed at 60000G for 30 minutes and the precipitates were recovered. After washing 3 times with KPB (10 mM potassium phosphate buffer solution, pH 7.0) supplemented with 1% NP-40, the precipitates were suspended in PBS containing 7.5 M urea. After centrifugation at 60000G for 30 minutes, the supernatant was recovered. The supernatant was fractionated by linear density gradient from 0M to 1M of NaCl concentration using QAE-TOYO PEARL COLUMN (manufactured by TOSO Co., Ltd.) which had been equilibrated with KPB having pH of 7.8 and containing 6M urea. The fraction containing TMG-1 was thus recovered at 0M of NaCl concentration. This fraction was further fractionated by linear density gradient from 0M to 1M of NaCl concentration using Red-TOYO PEARL COLUMN (manufactured by TOSO Co., Ltd.) which had been equilibrated with the same KPB as used for QAE-TOYO PEARL COLUMN. The fraction containing TMG-1 (about 200 μg) was thus recovered at 0.5M to 0.7M of NaCl concentration.

The thus obtained TTMG-1 was subjected to SDS-PAGE in a manner similar to Example 4. After staining with Brilliant Blue R-250, the purity was determined to be about 90% by TLC-scanner (TS-930: Shimadzu Seisakusho Ltd.).

From the culture broth of TG1, about 200 μg of TTMG-1 was purified.

Example 6

Growth inhibition of *Mycoplasma gallisepticum*

TTMG-1 obtained in Example 5 was dissolved in Dulbecco's PBS in a concentration of 200 μg/ml. After 1 ml of the solution was mixed with an equal volume of complete Freund adjuvant or aluminum hydroxide gel, the mixture was subcutaneously injected to chicken of 8 weeks age or older (line-M, SPF: Nihon Seibutsu Kagaku Kenkyusho) at the right thigh. Further 2 weeks after, 1 ml each of TTMG-1 described above was subcutaneously administered for the second immunization to chicken as in the first immunization. A week after, anti-TTMG-1 serum was collected from the heart of chicken.

On the other hand, *Mycoplasma gallisepticum* S6 strain inoculated by 10% on PPLO liquid medium (modified Chanock's medium). After incubation at 37° C. for 3 days, the culture broth was passed through a membrane filter of 0.45 μm to remove the agglutinated cells. The filtrate was diluted to a cell count of $10^3$ CFU/ml with PPLO liquid medium, which was used for determination of the activity.

The cell solution was separately charged by 400 μl each in a sterilized polypropylene tube. To the cell solution was added 100 μl each of standard chicken serum, TMG-1 immunized serum (Japanese Patent Application Laid-Open No. 2-111795) and TTMG-1 immunized serum. By culturing at 37° C. for 2 to 5 days, growth inhibition test was carried out.

On Days 0, 1, 2, 3 and 4 of the incubation, 10 each was collected from each culture broth for growth inhibition test of *Mycoplasma gallisepticum*. Each collected culture broth harvested was spread over a plate of PPLO agar medium followed by culturing at 37° C. for 7 days. The cell count in the corresponding culture broth was deduced from the number of colonies formed. The results of cell count on Day 3 are shown in Table 1.

TABLE 1

| Sample | Cell Count on Day 3 the number of cells |
| --- | --- |
| Standard chicken serum | $1.3 \times 10^8$ |
| Anti-TMG-1 chicken serum | $3.4 \times 10^6$ |
| Anti-TTMG-1 chicken serum | $1.8 \times 10^5$ |

When the added sample was standard chicken serum or the culture broth supplemented with horse serum, no difference was noted in the growth rate of *Mycoplasma gallisepticum* and the cell count reached the saturation on Day 3 of the incubation. In the culture broth supplemented with anti-TTMG-1 immunized chicken serum *Mycoplasma gallisepticum* immunized chicken serum or with *Mycoplasma gallisepticum* infected chicken serum, the growth of *Mycoplasma gallisepticum* was clearly inhibited on Day 3. The results indicate that TTMG-1 protein is an antigen which can induce the antibody capable of effectively inhibiting the growth of *Mycoplasma gallisepticum.*

Example 7

Effect of preventing infection of TTMG-1 immunized chicken with *Mycoplasma gallisepticum*

*Mycoplasma gallisepticum* KP-13 strain was cultured in PPLO liquid medium to reach a concentration of $1\times10^6$ CFU/ml. Two weeks after the second booster in the chicken immunized in Example 6, the cell solution was infranasaly inoculated in the nasal cavities by 0.5 ml each. Four days after the chicken was sacrificed and the infraorbital sinuses and the air sac were wiped with sterilized cotton applicators, respectively. The applicators were immersed in PPLO liquid medium (containing 1% penicillin and 0.05% thallium acetate), respectively, followed by stationary culture at 37° C. for 168 hours. After stationary culture of further 20 μl in 2 ml PPLO medium (containing 1% penicillin and 0.05% thallium acetate), the presence or absence of the bacteria was detected as in Example 6 to determine the effect of preventing infection.

The effect of preventing infection is shown in Table 2. The chicken inoculated with TTMG-1 of the present invention shows a marked effect of preventing infection as compared to non-immunized chicken, indicating that TTMG-1 of the present invention exhibits a remarkable vaccine effect.

TABLE 2

| Immune Antigen | Recovery of *Mycoplasma gallisepticum* Infraorbital sinuses |
|---|---|
| TTMG-1 | 5/10 |
| none | 4/5 |

What is claimed is:

1. A substantially pure protein capable of reacting with *Mycoplasma gallisepticum* immunized serum or *Mycoplasma gallisepticum* infected serum, said protein having the sequence of SEQ ID NO:4, or said protein having a bacteria-derived enzyme fused to the N-terminus of SEQ ID NO:4.

2. A protein according to claim 1 having a molecular weight of about 40 kilodaltons and having the sequence of SEQ ID NO:4.

3. A vaccine for *Mycoplasma gallisepticum* infection in poultry comprising as an effective ingredient a protein according to claim 1 or 2.

4. An isolated DNA comprising the DNA sequence of SEQ ID NO:1.

5. An isolated DNA sequence comprising the sequence of nucleotides 202–1352 of SEQ ID NO:1 or a degenerate sequence thereof.

6. A recombinant vector in which DNA fragment according to claim 5 is incorporated.

7. A host cell transformed by a recombinant vector according to claim 6.

* * * * *